US008155758B2

(12) United States Patent
Roline et al.

(10) Patent No.: US 8,155,758 B2
(45) Date of Patent: Apr. 10, 2012

(54) FAULT TOLERANT IMPLANTABLE PULSE GENERATORS AND IMPLANTABLE CARDIOVERTER-DEFIBRILLATORS INCORPORATING PHYSIOLOGIC SENSORS AND METHODS FOR IMPLEMENTING FAULT TOLERANCE IN SAME

(75) Inventors: Glenn M. Roline, Anoka, MN (US); Michael B. Terry, Camas, WA (US); Jonathan P. Roberts, Coon Rapids, MN (US); James D. Reinke, Maple Grove, MN (US); Robert A. Corey, Roseville, MN (US)

(73) Assignee: Medtronic, Inc., Minneapolis, MN (US)

(*) Notice: Subject to any disclaimer, the term of this patent is extended or adjusted under 35 U.S.C. 154(b) by 256 days.

(21) Appl. No.: 11/380,567

(22) Filed: Apr. 27, 2006

(65) Prior Publication Data
US 2007/0265669 A1 Nov. 15, 2007

Related U.S. Application Data

(60) Provisional application No. 60/745,789, filed on Apr. 27, 2006.

(51) Int. Cl.
*A61N 1/37* (2006.01)
(52) U.S. Cl. ............ 607/119; 607/6; 607/17; 607/36
(58) Field of Classification Search ............ 607/36, 607/17–24, 119, 6
See application file for complete search history.

(56) References Cited

U.S. PATENT DOCUMENTS

| 4,445,512 A * | 5/1984 | Krupka et al. ............ 607/29 |
| 4,791,931 A * | 12/1988 | Slate ............ 607/24 |
| 4,791,935 A | 12/1988 | Baudino et al. |
| 4,803,049 A * | 2/1989 | Hirschfeld et al. ............ 422/58 |
| 4,807,629 A * | 2/1989 | Baudino et al. ............ 607/22 |
| 5,564,434 A | 10/1996 | Halperin et al. |
| 5,904,708 A * | 5/1999 | Goedeke ............ 607/18 |
| 6,144,866 A * | 11/2000 | Miesel et al. ............ 600/333 |
| 6,250,309 B1 | 6/2001 | Krichen et al. |
| 6,254,525 B1 * | 7/2001 | Reinhardt et al. ............ 600/17 |
| 6,497,655 B1 | 12/2002 | Linberg et al. |
| 2006/0064149 A1 * | 3/2006 | Belacazar et al. ............ 607/122 |

OTHER PUBLICATIONS

"Fault Tolerant Design Approaches and Fault Detection Techniques Used for Sensor Based Products", 9 pp.

* cited by examiner

*Primary Examiner* — Niketa Patel
*Assistant Examiner* — Joseph Dietrich
(74) *Attorney, Agent, or Firm* — Reed A. Duthler; Stephen W. Bauer (57) ABSTRACT

This disclosure relates to fault tolerant instantiations of a cardiac therapy delivery device such as an implantable cardiac stimulator (e.g., an implantable pulse generator, IPG, and/or an implantable cardioverter-defibrillator, ICD) coupled to an implantable physiologic sensor (IPS). According to the disclosure delivery of cardiac pacing and/or cardioversion-defibrillator therapy delivery can cause errors in output signals from an IPS. Resolution of such errors involves selectively energizing (or disconnecting the output signal from) the IPS during pacing and/or defibrillation therapy delivery. Programmable signal "blanking" in lieu of or in addition to the foregoing also improves the integrity of the output signal (i.e., continuously energize the IPS and ignore parts of the output signal). An ICD having a transient weakness in an insulated conductor used for the IPS signal can likewise have the IPS de-energized and/or blank the IPS output signal during high voltage therapy delivery.

29 Claims, 6 Drawing Sheets

FAULT TOLERANT IMPLANTABLE PULSE GENERATORS AND IMPLANTABLE CARDIOVERTER-DEFIBRILLATORS INCORPORATING PHYSIOLOGIC SENSORS AND METHODS FOR IMPLEMENTING FAULT TOLERANCE IN SAME

CROSS REFERENCE AND INCORPORATION BY REFERENCE

This patent disclosure relates to provisional patent application filed on even date hereof; namely, application Ser. No. 60/745,789 entitled, "FAULT TOLERANT SENSORS AND METHODS FOR IMPLEMENTING FAULT TOLERANCE IN IMPLANTABLE MEDICAL DEVICES," the entire contents, including exhibits appended thereto, are hereby incorporated herein by reference.

FIELD OF THE INVENTION

The invention relates generally to fault tolerant implantable physiologic sensor (IPS) units that operatively couple to circuitry within an active implantable medical device (AIMD), such as an implantable pulse generator (IPG) circuitry and/or implantable cardioverter-defibrillators (ICD) circuitry for delivering therapy to cardiac tissue.

BACKGROUND OF THE INVENTION

Implantable medical devices are used to monitor, diagnose, and/or deliver therapies to patients suffering from a variety of conditions. Exemplary AIMDs include implantable pulse generators (IPGs) including pacemakers, gastric, nerve, brain and muscle stimulators, implantable drug pumps, and the like that optionally include implantable cardioverter-defibrillator (ICD) circuitry.

Due in part to the fact that an implantable physiologic sensor (IPS) coupled to an AIMD is exposed to electrical stimulation during therapy delivery there exists a need for tolerance to the corresponding noise and signal degradation accompanying such therapy delivery that could cause system failures, incorrect and/or improper operation. Among other things, certain forms, aspects and embodiments of the present invention provide improved and more predictable and reliable performance of an IPS coupled to an AIMD during AIMD therapy delivery.

BACKGROUND

There are many situations in which a patient requires long-term monitoring and when it may be desirable to implant a sensor for monitoring within the body of the patient. One such monitor is a pressure monitor, which can measure the pressure at a site in the body, such as a blood vessel or a chamber of the heart. When implanted in a vessel or a heart chamber, the sensor responds to changes in blood pressure at that site. Blood pressure is measured most conveniently in units of millimeters of mercury (mm Hg) (1 mm Hg=133 Pa).

The implanted pressure sensor is coupled to an implanted medical device, which receives analog signals from the sensor and processes the signals. Signals from the implanted pressure sensor may be affected by the ambient pressure surrounding the patient. If the patient is riding in an airplane or riding in an elevator in a tall building, for example, the ambient pressure around the patient may change. Changes in the ambient pressure affect the implanted pressure sensor, and may therefore affect the signals from the pressure sensor.

A typical implanted device that employs a pressure sensor is not concerned with total pressure, i.e., blood pressure plus ambient pressure. Rather, the device typically is designed to monitor blood pressure at the site of the internal sensor. To provide some compensation for changes in ambient pressure, some medical devices take additional pressure measurements with an external pressure sensor. The external pressure sensor, which may be mounted outside the patient's body, responds to changes in ambient pressure, but not to changes in blood pressure. The blood pressure is a function of the difference between the signals from the internal and external pressure sensors.

Although the internal pressure sensor may generate analog pressure signals as a function of the pressure at the monitoring site, the pressure signals are typically converted to digital signals, i.e., a set of discrete binary values, for digital processing. An analog-to-digital (A/D) converter receives an analog signal, samples the analog signal, and converts each sample to a discrete binary value. In other words, the pressure sensor generates a pressure signal as a function of the pressure at the monitoring site, and the A/D converter maps the pressure signal to a binary value.

The A/D converter can generate a finite number of binary values. An 8-bit A/D converter, for example, can generate 256 discrete binary values. The maximum binary value corresponds to a maximum pressure signal, which in turn corresponds to a maximum pressure at the monitoring site. Similarly, the minimum binary value corresponds to a minimum pressure signal, which in turn corresponds to a minimum site pressure. Accordingly, there is a range of pressure signals, and therefore a range of site pressures, that can be accurately mapped to the binary values.

In a patient, the actual site pressures are not constrained to remain between the maximum and minimum monitoring site pressures. Due to ambient pressure changes or physiological factors, the pressure sensor may experience a site pressure that is "out of range," i.e., greater than the maximum monitoring site pressure or less than the minimum monitoring site pressure. In response to an out-of-range pressure, the pressure sensor generates an analog signal that is greater than the maximum pressure signal or less than the minimum pressure signal. An out-of-range pressure cannot be mapped accurately to a binary value. For example, the pressure sensor may experience a high pressure at the monitoring site that exceeds the maximum site pressure. In response, the pressure signal generates a pressure signal that exceeds the maximum pressure signal. The pressure signal is sampled and the data samples are supplied to the A/D converter. When the A/D converter receives a data sample that is greater than the maximum pressure signal, the A/D converter maps the data sample to a binary value that reflects the maximum pressure signal, rather than the true value of the data sample. In other words, the data sample is "clipped" to the maximum binary value. Similarly, when the A/D converter receives a data sample that is below the minimum pressure signal, the converter generates a binary value that reflects the minimum pressure signal rather than the true value of the data sample.

Because of changes in ambient pressure, pressures sensed by the internal pressure sensor may be in range at one time and move out of range at another time. When the pressures move out of range, some data associated with the measured pressures may be clipped, and some data reflecting the true site pressures may be lost. In such a case, the binary values may not accurately reflect the true blood pressures at the monitoring site.

To avoid clipping, the implanted device may be programmed to accommodate an expected range of site pressures. Estimating the expected range of site pressures is difficult, however, because ambient pressure may depend upon factors such as the weather, the patient's altitude and the patient's travel habits. Pressures may be in range when the patient is in one environment, and out of range when the patient is in another environment.

The risk of clipping can further be reduced by programming the implanted device with a high maximum site pressure that corresponds to the maximum binary value and with a low minimum site pressure that corresponds to the minimum binary value. Programming the device for a high maximum and a low minimum creates a safety margin. The price of safety margins, however, is a loss of sensitivity. Safety margins mean that pressures near the maximum and minimum site pressures are less likely to be encountered. As a result, many of the largest and smallest binary values are less likely to be used, and the digital data is a less precise representation of the site pressures.

BRIEF SUMMARY OF THE INVENTION

The present invention provides one or more structures, techniques, components and/or methods for avoiding or positively resolving one or more possible failure modes for a chronically implanted medical device that couples to one or more sensors.

One aspect of the invention relates to fault tolerant instantiations of a cardiac therapy delivery device such as an implantable cardiac stimulator (e.g., an implantable pulse generator, IPG, and/or an implantable cardioverter-defibrillator, ICD) coupled to an implantable physiologic sensor (IPS). According to the disclosure delivery of cardiac pacing and/or cardioversion-defibrillator therapy delivery can cause errors in output signals from an IPS. Resolution of such errors involves selectively energizing (or disconnecting the output signal from) the IPS during pacing and/or defibrillation therapy delivery. Programmable signal "blanking" in lieu of or in addition to the foregoing also improves the integrity of the output signal (i.e., continuously energize the IPS and ignore parts of the output signal). An ICD having a transient weakness in an insulated conductor used for the IPS signal can likewise have the IPS de-energized and/or blank the IPS output signal during high voltage therapy delivery.

In related embodiments of the invention, a possible fault scenario includes a breach of an outer layer of insulation on an elongated medical electrical lead which couples a circuit-bearing, active AIMD disposed within a substantially hermetic housing to a sensor disposed within a sensor capsule. In this embodiment the AIMD provides only physiological sensing of a patient parameter, such as endocardial pressure. In one form of the invention, the sensor comprises an absolute pressure sensor adapted for chronic implantation within a portion of a right ventricle (RV) of a patient. The portion could include the RV outflow tract (RVOT) which is a region of relatively high-rate blood flow which correspondingly requires a robust sensor capsule and coupling to a medical electrical lead coupled thereto. On type of mitigation for this embodiment involves an electrical coupling between a distal tip portion of the medical lead, the optionally electrically conducting sensor capsule, and an electrical reference for the circuitry within the AIMD housing. The result is that no electrical current can flow from the device to the patient, while maintaining the functionality of the AIMD in vivo.

Of course, one aspect of the invention involves the ability to maintain AIMD functionality and avoid the possibility of having to explant the AIMD from the patient as well as the oftentimes accompanying possibility of complications due to an explant procedure.

In another aspect, an AIMD includes a chronically implantable physiologic sensor (IPS) and is configured to sense a physiologic parameter of a patient (e.g., blood pressures, acceleration, pH levels, lactate, saturated oxygen, blood sugar, calcium, potassium, sodium, etc.) and provide a therapy such as cardiac pacing, high-energy cardioversion/defibrillation therapy and/or a drug or substance delivery regimen or the like. For example, in an AIMD including an IPS can chronically measure blood pressure, provide cardiac pacing therapy and, as appropriate, deliver high-energy defibrillation therapy. However, during delivery of electrical stimulation to a subject the output signals from and/or the power supplied to the IPS can become degraded or otherwise fail to correspond to the actual physiologic condition of the subject. In this embodiment, blanking the output signal and/or selectively providing power to the IPS is used to avoid processing the degraded or non-corresponding output signal.

In addition to the foregoing therapy delivery devices, the AIMD can comprise an IPG configured to delivery cardiac resynchronization therapy (CRT) to a patient suffering from cardiac dysfunction, including symptoms of mild to advanced heart failure. In one form of this embodiment, the sensor capsule can be adapted to sense left lateral wall acceleration from a medical electrical pacing lead disposed within a portion of the great vein or an epicardial location for activation of the left ventricle (LV). Another pacing lead is adapted to couple to one of the atrial chambers (RA,LA) and yet another pacing lead is adapted to couple to an activation site of the RV. In this form of the invention a fault mitigation structure again involves selectively energizing and/or blanking the output signal from the accelerometer. Due to the likelihood for diverse atrial and/or temporally offset bi-ventricular pacing therapy delivery longer blanking windows and/or reduced duty cycle for the IPS could be required.

DETAILED DESCRIPTION

Figure 1:
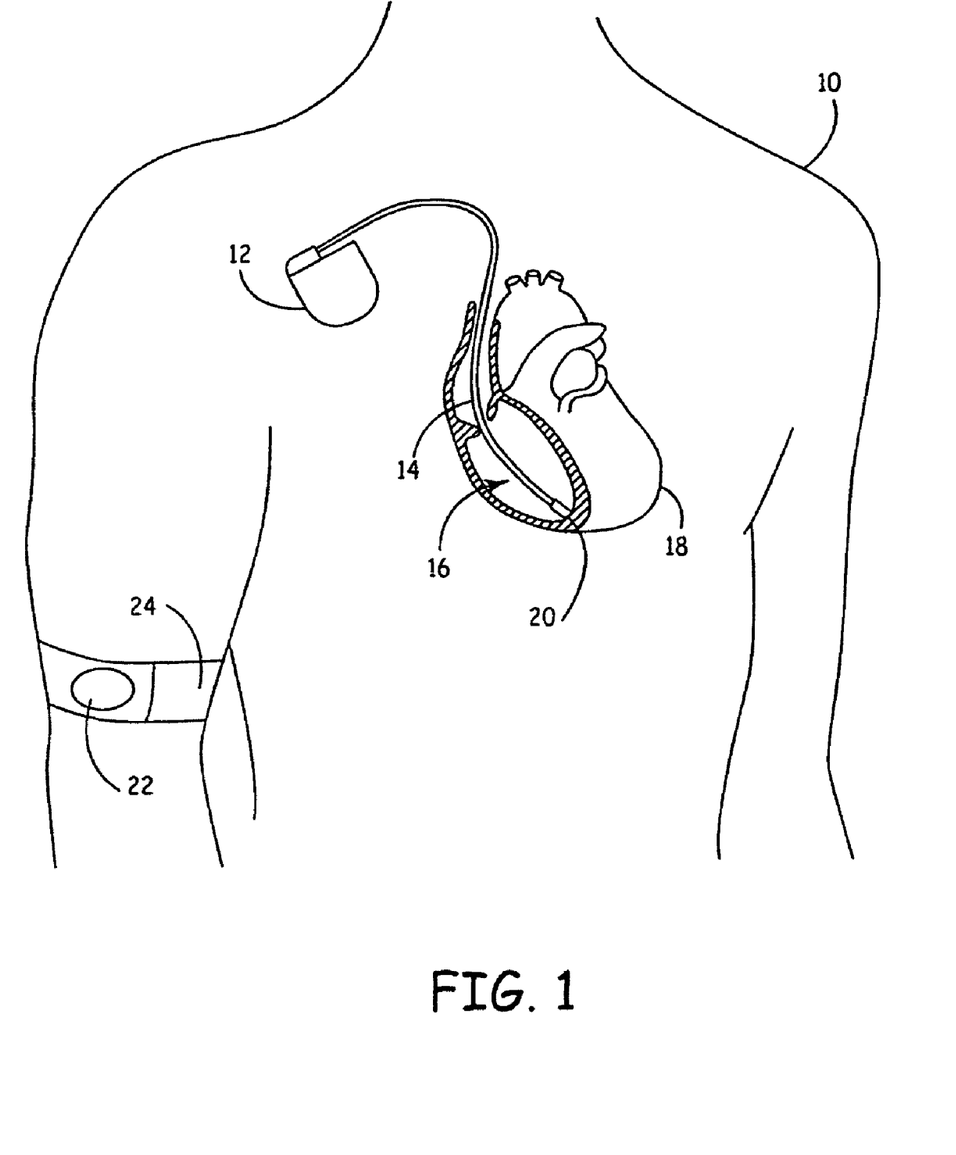
FIG. 1 is a diagram of a human body with an implanted medical device and pressure sensors.

FIG. 1 is a diagram of a body of a patient 10 having an implantable medical device (AIMD) 12 according to one embodiment of the present invention. As depicted in FIG. 1 lead 14 operatively couples to circuitry (not shown) within the AIMD 12 and extends into the right ventricle 16 of the heart 18. A chronically implantable pressure sensor 20 is shown disposed within a portion of a right ventricle (RV) 16 and couples to lead 14. The pressure sensor 20 monitors and measures changes in blood pressure in the RV 16. The blood pressure in RV 16 is a function of factors such as the volume of RV 16, the pressure exerted by the contraction of heart 18 and the ambient pressure around patient 10 and the blood pressure varies throughout the cardiac cycle as is well known in the art. While a pressure sensor 20 is depicted in FIG. 1 diverse other sensors can directly benefit from the teaching of the present invention as noted hereinabove.

In one form of the invention the AIMD 12 receives analog signals from the implanted pressure sensor 20 via lead 14 although digital sensors and/or circuitry can be utilized in conjunction with the invention. As noted, in the depicted embodiment the signals are a function of the pressure sensed by implanted pressure sensor 20 at the monitoring site (e.g. RV 16) which can of course include myriad different locations on or about the heart and other muscles, circulatory system, nervous system, digestive system, skeleton, brain, diverse organs, and the like. In the depicted embodiment, patient 10 carries or otherwise provides or maintains access to an external pressure sensor or reference 22 which is used to correct the readings of the implanted absolute-type pressure sensor 20. FIG. 1 depicts external pressure sensor 22 coupled to a belt or strap 24 coupled to the arm of patient 10, but this is but one of many possible sites for external pressure sensor 22. The external pressure sensor 22 responds to changes in ambient pressure, and is unaffected by blood pressure in the RV 16. The AIMD 12 receives signals from external pressure sensor 22 via communication such as radio frequency (RF) telemetry. Alternatively, the AIMD 12 need not communicate with external pressure sensor 22 in any way.

Figure 2:
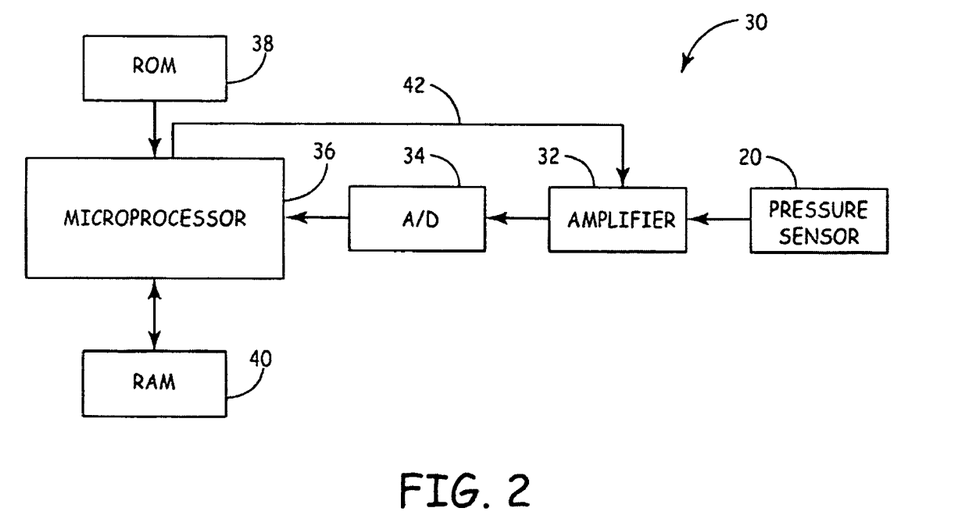
FIG. 2 is a simplified block diagram illustrating an exemplary system that implements the an embodiment of the invention wherein a physiologic sensor provides chronic monitoring and diagnostic for a patient.

The AIMD 12 optionally includes a digital processor. Thus, the analog signals from implanted pressure sensor 20 are converted to digital signals for processing. Referring briefly to FIG. 2, the analog signals are first amplified by an amplifier 32 and are sampled and are mapped to discrete binary values by an A/D converter 34. Each binary value corresponds to a pressure signal that in turn corresponds to a site pressure. The A/D converter 34 maps each sample to a binary value that corresponds most closely to the actual pressure signal and site pressure reflected by the sample.

The sensitivity of AIMD 12 to changes in pressure is a function of the range of pressures that map to a single binary value. The smaller the pressure change represented by consecutive binary values, the more sensitive implanted medical device 12 is to changes in pressure. For example, an 8-bit A/D converter may be configured to map pressures between a minimum site pressure of 760 mm Hg and a maximum site pressure of 860 mm Hg to discrete binary values. In this example, a one-bit increase represents a pressure increase of about 0.4 mm Hg.

In a conventional implanted medical device, there may be a tradeoff between range and sensitivity. When the number of possible discrete binary values is fixed, expanding the range of site pressures that are represented by the binary values results in a decrease in sensitivity, because a one-bit change represents a larger pressure change. Similarly, decreasing the range results in an increase in sensitivity because a one-bit change represents a smaller pressure change.

In an illustrative example, an 8-bit A/D converter may be configured to map pressures between 760 mm Hg and 860 mm Hg to discrete binary values, with a one-bit increase representing a pressure increase of about 0.4 mm Hg. When the same 8-bit A/D converter is configured to map pressures between 746 mm Hg and 874 mm Hg to discrete binary values, the overall range of site pressures that can be mapped to binary values expands by 128 mm Hg. The sensitivity, however, decreases. A one-bit increase represents a pressure increase of 0.5 mm Hg.

Not all changes to range affect sensitivity. In some circumstances, a range may be offset without affecting sensitivity. In an offset, the minimum site pressure and the maximum site pressure are increased or decreased by the same amount. For example, a 8-bit A/D converter may be configured to map pressures between 760 mm Hg and 860 mm Hg to discrete binary values, with a one-bit increase representing a pressure increase of about 0.4 mm Hg. When the pressure range is shifted downward to pressures between 740 mm Hg and 840 mm Hg, the range is offset but not expanded. When the range is offset, sensitivity is not affected. A one-bit increase still represents a pressure increase of about 0.4 mm Hg.

Implanted medical device 12 implements techniques for automatically adjusting mapping parameters in response to changes in pressure conditions. In particular, implanted medical device 12 periodically evaluates the digital pressure data to determine whether pressure data may be going out of range, and expands and/or offsets the range to avoid having data go out of range. In addition, implanted medical device 12 determines whether the range can be decreased so that sensitivity can be enhanced.

FIG. 2 is a block diagram of an exemplary system 30 that implements the invention. Pressure sensor 20 supplies an analog pressure signal to amplifier 32. The analog pressure signal is a function of the site pressure, where pressure sensor 20 is disposed. The analog pressure signal may be, for example, a voltage signal. Amplifier 32 amplifies the signal by, for example, amplifying the voltage. Amplifier 32 may perform other operations such as serving as an anti-aliasing filter. Amplifier 32 has an adjustable gain and an adjustable offset. The gain and offset of amplifier 32 are adjustable under the control 42 of a controller, which may take the form of a microprocessor 36. The controller may take other forms, such as an application-specific integrated circuit (ASIC), a field programmable gate array (FPGA), or any other circuit including discrete and/or integrated components and that has control capabilities.

Amplifier 32 supplies the amplified analog signal to A/D converter 34. The range and resolution of pressure signals supplied to A/D converter 34 is a function of the gain of amplifier 32 and the offset of amplifier 32. By adjusting the gain and/or offset of amplifier 32, microprocessor 36 regulates the mapping parameters; that is, the correspondence between site pressures and binary values. A/D converter 34 samples the pressure signals from amplifier 32 and converts the samples into discrete binary values, which are supplied to microprocessor 36. In this way, microprocessor 36, amplifier 32 and A/D converter 34 cooperate to map the site pressures to binary values.

The number of possible discrete binary values that can be generated by A/D converter 34 is fixed. When there is a risk of data out of range, it is not feasible to increase the number of binary values that represent the site pressures. As will be described in more detail below, microprocessor 36 adjusts the gain and/or the offset of amplifier 32 so that the data remain in range and so that the digital pressure data generated by A/D converter 34 accurately reflect the site pressures sensed with pressure sensor 20.

Microprocessor 36 processes the digital pressure data according to algorithms embodied as instructions stored in memory units such as read-only memory (ROM) 38 or random access memory (RAM) 40. Microprocessor 36 may, for example, control a therapy delivery system (not shown in FIG. 2) as a function of the digital pressure data.

Microprocessor 36 may further compile statistical information pertaining to the digital pressure data. In one embodiment, microprocessor 36 generates a histogram of the digital pressure data. The histogram, which may be stored in RAM 40, reflects the distribution of pressures sensed by pressure sensor 20.

The histogram includes a plurality of "bins," i.e., a plurality of numbers of digital data samples of comparable magnitude. For example, a histogram that stores the number of digital values corresponding to pressures between 760 mm Hg and 860 mm Hg may include twenty bins, with each bin recording the number of data samples that fall in a 5 mm Hg span. The first bin holds the number of values between 760 mm Hg and 765 mm Hg, while the second bin holds the number of values between 765 mm Hg and 770 mm Hg, and so on. More or fewer bins may be used.

The distribution of values in the bins provides useful information about the pressures in right ventricle 16. Data accumulates in the histogram over a period of time called a "storage interval," which may last a few seconds, a few hours or a few days. At the end of the storage interval, microprocessor 36 stores in RAM 40 information about the distribution of pressures, such as the mean, the standard deviation, or pressure values at selected percentiles. Microprocessor 36 may then clear data from the histogram and begin generating a new histogram.

When microprocessor 36 adjusts the mapping parameters, the new histogram may be different from the preceding histogram. In particular, the new histogram may record the distribution of an expanded range of pressure data, or a reduced range of pressure data, or a range that has been offset up or down. In general, the adjustments to the mapping parameters tend to center the distribution in the histogram, and tends to reduce the number of values in the highest and lowest bins. Microprocessor 36 adjusts the mapping parameters based upon the distribution of digital pressure data in the preceding histogram. Microprocessor 36 may make the adjustments to avoid data out of range, to avoid having unused range, or both.

In one embodiment of the invention, microprocessor 36 senses the possibility of out-of-range data or unused range by sensing the contents of the boundary bins of the histogram, for example by checking whether the data distribution has assigned values to the bins that accumulate the lowest values and the highest values of the histogram. As a result of checking the bins, microprocessor 36 may automatically adjust the gain, or the offset, or both of amplifier 32.

Figure 3:
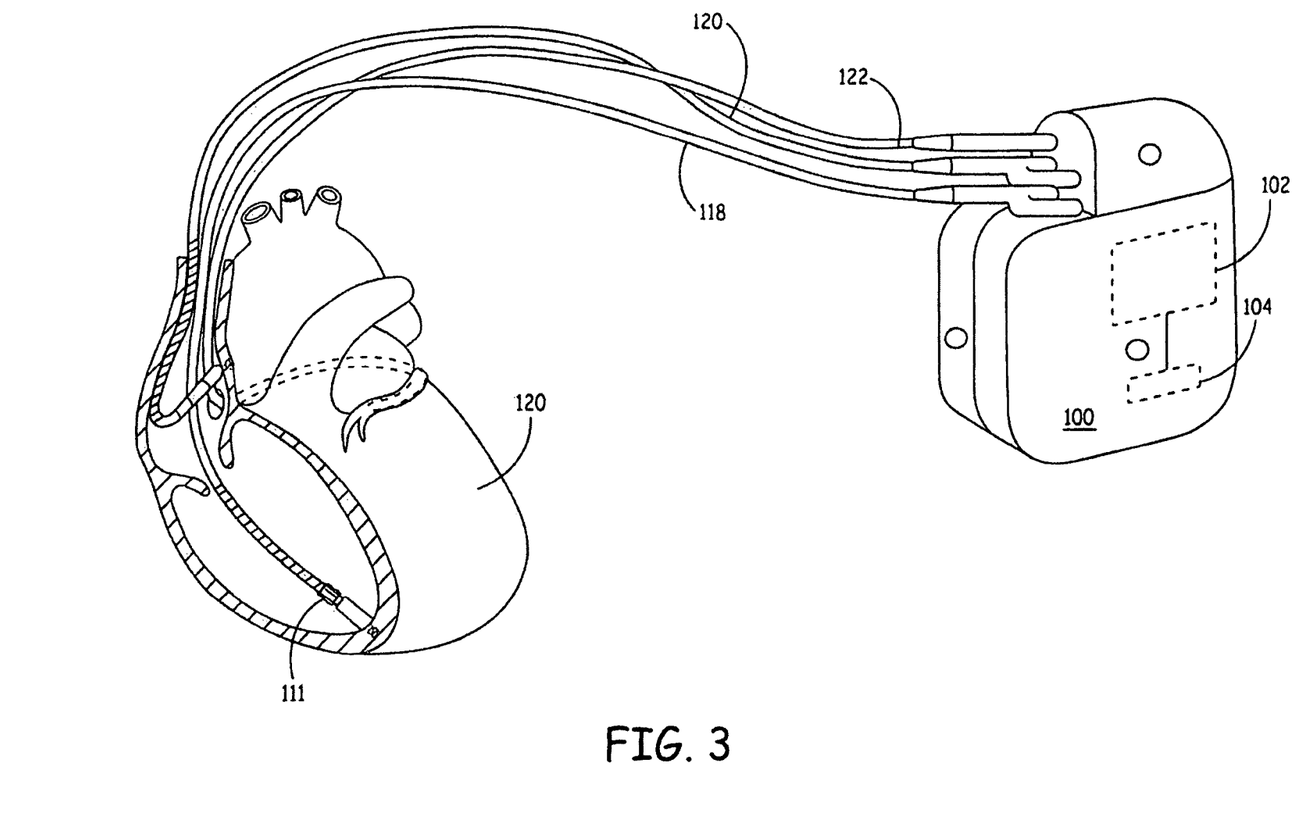
FIG. 3 is an illustration of an exemplary implantable medical device (AIMD) connected to monitor a patient's heart.

FIG. 3 is an illustration of an exemplary AIMD 100 configured to deliver bi-ventricular, triple chamber cardiac resynchronization therapy (CRT) wherein AIMD 100 fluidly couples to monitor cardiac electrogram (EGM) signals and blood pressure developed within a patient's heart 120. The AIMD 100 may be configured to integrate both monitoring and therapy features, as will be described below. AIMD 100 collects and processes data about heart 120 from one or more sensors including a pressure sensor and an electrode pair for sensing EGM signals. AIMD 100 may further provide therapy or other response to the patient as appropriate, and as described more fully below. As shown in FIG. 3, AIMD 100 may be generally flat and thin to permit subcutaneous implantation within a human body, e.g., within upper thoracic regions or the lower abdominal region. AIMD 100 is provided with a hermetically-sealed housing that encloses a processor 102, a digital memory 104, and other components as appropriate to produce the desired functionalities of the device. In various embodiments, AIMD 100 is implemented as any implanted medical device capable of measuring the heart rate of a patient and a ventricular or arterial pressure signal, including, but not limited to a pacemaker, defibrillator, electrocardiogram monitor, blood pressure monitor, drug pump, insulin monitor, or neurostimulator. An example of a suitable AIMD that may be used in various exemplary embodiments is the CHRONICLE® implantable hemodynamic monitor (IHM) device available from Medtronic, Inc. of Minneapolis, Minn., which includes a mechanical sensor capable of detecting a pressure signal.

In a further embodiment, AIMD 100 comprises any device that is capable of sensing a pressure signal and providing pacing and/or defibrillation or other electrical stimulation therapies to the heart. Another example of an AIMD capable of sensing pressure-related parameters is described in commonly assigned U.S. Pat. No. 6,438,408B1 issued to Mulligan et al. on Aug. 20, 2002.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 3, AIMD 100 may receive one or more cardiac leads for connection to circuitry enclosed within the housing. In the example of FIG. 3, AIMD 100 receives a right ventricular endocardial lead 118, a left ventricular coronary sinus lead 122, and a right atrial endocardial lead 120, although the particular cardiac leads used will vary from embodiment to embodiment. In addition, the housing of AIMD 100 may function as an electrode, along with other electrodes that may be provided at various locations on the housing of AIMD 100. In alternate embodiments, other data inputs, leads, electrodes and the like may be provided. Ventricular leads 118 and 122 may include, for example, pacing electrodes and defibrillation coil electrodes (not shown) in the event AIMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies. AIMD 100 obtains pressure data input from a pressure sensor that is carried by a lead such as right ventricular endocardial lead 118. AIMD 100 may also obtain input data from other internal or external sources (not shown) such as an oxygen sensor, pH monitor, accelerometer or the like.

In operation, AIMD 100 obtains data about heart 120 via leads 118, 120, 122, and/or other sources. This data is provided to processor 102, which suitably analyzes the data, stores appropriate data in memory 104, and/or provides a response or report as appropriate. Any identified cardiac episodes (e.g. an arrhythmia or heart failure decompensation) can be treated by intervention of a physician or in an automated manner. In various embodiments, AIMD 100 activates an alarm upon detection of a cardiac event or a detected malfunction of the AIMD. Alternatively or in addition to alarm activation, AIMD 100 selects or adjusts a therapy and coordinates the delivery of the therapy by AIMD 100 or another appropriate device. Optional therapies that may be applied in various embodiments may include drug delivery or electrical stimulation therapies such as cardiac pacing, resynchronization therapy, extra systolic stimulation, neurostimulation.

Figure 4:
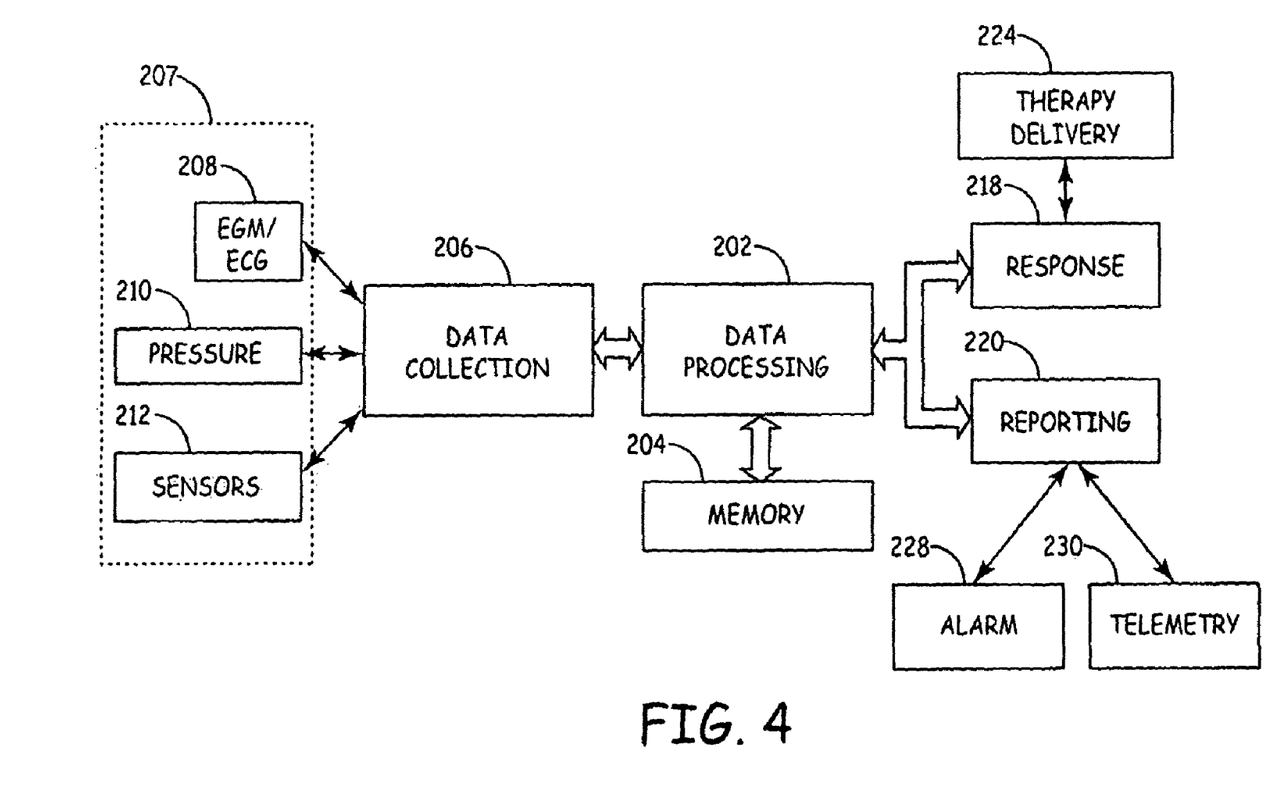
FIG. 4 is a block diagram summarizing the data acquisition and processing functions appropriate for practicing the invention.

FIG. 4 is a block diagram summarizing the data acquisition and processing functions appropriate for practicing the invention. The functions shown in FIG. 4 may be implemented in an AIMD system, such as AIMD 100 shown in FIG. 3. Alternatively, the functions shown in FIG. 4 may be implemented in an external monitoring system that includes sensors coupled to a patient for acquiring pressure signal data. The system includes a data collection module 206, a data processing module 202, a response module 218 and/or a reporting module 220. Each of the various modules may be implemented with computer-executable instructions stored in memory 104 and executing on processor 102 (shown in FIG. 3), or in any other manner.

The exemplary modules and blocks shown in FIG. 4 are intended to illustrate one logical model for implementing an AIMD 100, and should not be construed as limiting. Indeed, the various practical embodiments may have widely varying software modules, data structures, applications, processes and the like. As such, the various functions of each module may in practice be combined, distributed or otherwise differently-organized in any fashion across a patient monitoring system. For example, a system may include an implantable pressure sensor and EGM circuit coupled to an AIMD used to acquire pressure and EGM data, an external device in communication with the AIMD to retrieve the pressure and EGM data and coupled to a communication network for transferring the pressure and EGM data to a remote patient management center for analysis. Examples of remote patient monitoring systems in which aspects of the present invention could be implemented are generally disclosed in U.S. Pat. No. 6,497,655 issued to Linberg and U.S. Pat. No. 6,250,309 issued to Krichen et al., both of which patents are incorporated herein by reference in their entirety.

Pressure sensor 210 may be deployed in an artery for measuring an arterial pressure signal or in the left or right ventricle for measuring a ventricular pressure signal. In some embodiments, pressure sensor 210 may include multiple pressure sensors deployed at different arterial and/or ventricular sites. Pressure sensor 210 may be embodied as the pressure sensor disclosed in commonly assigned U.S. Pat. No. 5,564,434, issued to Halperin et al., hereby incorporated herein in its entirety.

Data sources 207 may include other sensors 212 for acquiring physiological signals useful in monitoring a cardiac condition such as an accelerometer or wall motion sensor, a blood flow sensor, a blood gas sensor such as an oxygen sensor, a pH sensor, or impedance sensors for monitoring respiration, lung wetness, or cardiac chamber volumes. The various data sources 207 may be provided alone or in combination with each other, and may vary from embodiment to embodiment.

Data collection module 206 receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 translates the analog signals to digital equivalents using an analog-to-digital conversion scheme. Data collection module 206 may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 of FIG. 3 or another external processor.

Reporting module 220 is any circuit or routine capable of producing appropriate feedback from the AIMD to the patient or to a physician. In various embodiments, suitable reports might include storing data in memory 204, generating an audible or visible alarm 228, producing a wireless message transmitted from a telemetry circuit 230.

In a further embodiment, the particular response provided by reporting module 220 may vary depending upon the severity of the hemodynamic change. Minor episodes may result in no alarm at all, for example, or a relatively non-obtrusive visual or audible alarm. More severe episodes might result in a more noticeable alarm and/or an automatic therapy response.

When the functionality diagramed in FIG. 4 is implemented in an AIMD, telemetry circuitry 230 is included for communicating data from the AIMD to an external device adapted for bidirectional telemetric communication with AIMD. The external device receiving the wireless message may be a programmer/output device that advises the patient, a physician or other attendant of serious conditions (e.g., via a display or a visible or audible alarm). Information stored in memory 204 may be provided to an external device to aid in diagnosis or treatment of the patient. Alternatively, the external device may be an interface to a communications network such that the AIMD is able to transfer data to an expert patient management center or automatically notify medical personnel if an extreme episode occurs.

Response module 218 comprises any circuit, software application or other component that interacts with any type of therapy-providing system 224, which may include any type of therapy delivery mechanisms such as a drug delivery system, neurostimulation, and/or cardiac stimulation. In some embodiments, response module 218 may alternatively or additionally interact with an electrical stimulation therapy device that may be integrated with an AIMD to deliver pacing, extra systolic stimulation, cardioversion, defibrillation and/or any other therapy. Accordingly, the various responses that may be provided by the system vary from simple storage and analysis of data to actual provision of therapy in various embodiments.

The various components and processing modules shown in FIG. 4 may be implemented in an AIMD 100 (e.g., as depicted in FIG. 1 or 3) and housed in a common housing such as that shown in FIG. 3. Alternatively, functional portions of the system shown in FIG. 4 may be housed separately. For example, portions of the therapy delivery system 224 could be integrated with AIMD 100 or provided in a separate housing, particularly where the therapy delivery system includes drug delivery capabilities. In this case, response module 218 may interact with therapy delivery system 224 via an electrical cable or wireless link.

Figure 5A:
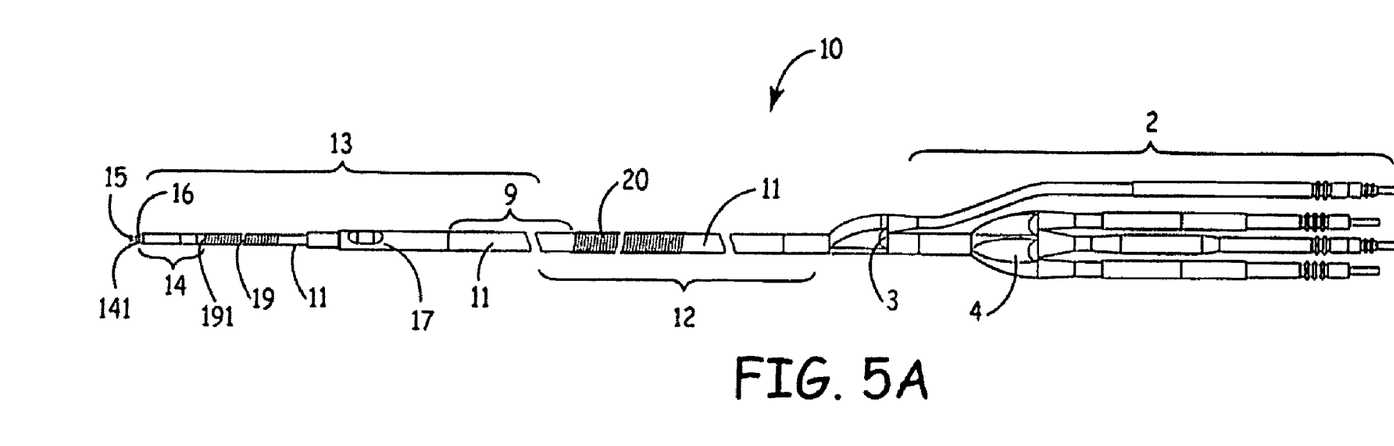
FIGS. 5A and 5B are elevational side views depicting a pair of exemplary medical electrical leads wherein in FIG. 5A a pair of defibrillation coils are disposed with a sensor capsule intermediate the coils and in FIG. 5B the sensor capsule is disposed distal the coils.
Figure 5B:
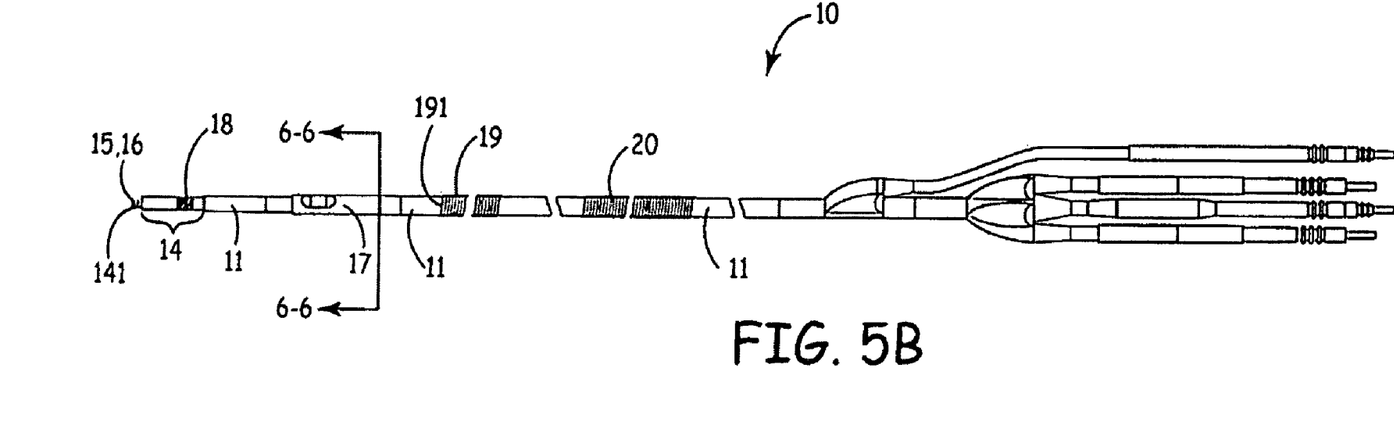

Referring now to FIGS. 5A and 5B which are elevational side views depicting a pair of exemplary medical electrical leads 10 wherein in FIG. 5A a pair of defibrillation coils 19,20 are disposed with a sensor capsule 17 intermediate the coils 19,20 and in FIG. 5B the sensor capsule 17 is disposed distal the coils 19,20. FIGS. 5A-B illustrate fixation element 15 as a distally extending helix, however element 15 may take on other forms, such as tines or barbs, and may extend from distal tip 14 at a different position and in a different direction, so long as element 15 couples lead body 11 to an endocardial surface of the heart in such a way to accommodate positioning of defibrillation electrode 19 and sensor 17 appropriately.

According to alternate embodiments of the present invention, sensor 17 is selected from a group of physiological sensors, which should be positioned in high flow regions of a circulatory system in order to assure proper function and long term implant viability of the sensor; examples from this group are well known to those skilled in the art and include, but are not limited to oxygen sensors, pressure sensors, flow sensors and temperature sensors. Commonly assigned U.S. Pat. No. 5,564,434 describes the construction of a pressure and temperature sensor and means for integrating the sensor into an implantable lead body. Commonly assigned U.S. Pat. No. 4,791,935 describes the construction of an oxygen sensor and means for integrating the sensor into an implantable lead body. The teachings U.S. Pat. Nos. 5,564,434 and 4,791,935, which provide means for constructing some embodiments of the present invention, are incorporated by reference herein. These drawings illustrate lead body 11 joined to connector legs 2 via a first transition sleeve 3 and a second transition sleeve 4; connector legs 2 are adapted to electrically couple electrodes 15, 16, 19 and 20 and sensor 17 to an IMD in a manner well known to those skilled in the art. Insulated electrical conductors, not shown, coupling each electrode 15, 16, 19 and 20 and sensor 17 to connector legs 2, extend within lead body 11. Arrangements of the conductors within lead body 11 include coaxial positioning (at least up to the sensor capsule 17), non-coaxial positioning and a combination thereof; according to one exemplary embodiment, lead body 11 is formed in part by a silicone or polyurethane multilumen tube, wherein each lumen carries one or more conductors.

Figure 6:
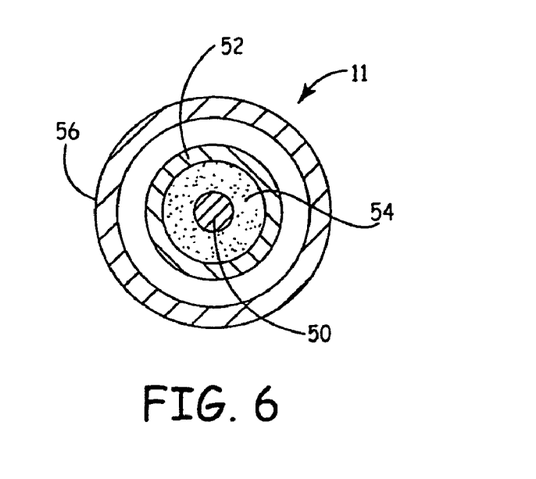
FIG. 6 is a cross sectional view of a coaxial conductor adapted for use with an implantable sensor.

FIG. 6 is a cross sectional view of a coaxial conductive lead body 11 adapted for operative coupling proximal of a sensor capsule taken along the line 6-6 of FIG. 5B according to the invention. In FIG. 6, an inner conductor 50 is spaced from an outer conductor 52 with an insulative material 54 disposed therebetween. The exterior of the biocompatible outer insulation 56 of the lead body 11 shields the conductors 50,52 from contact with conductive body fluid. One aspect of the instant invention involves failure of the outer insulation 56 and ways to render such a failure essentially innocuous to a patient.

Figure 7:
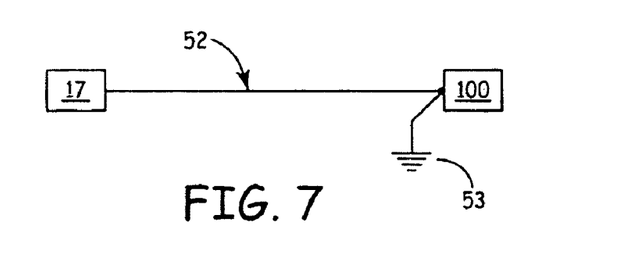
FIG. 7 is a schematic illustration of a sensor capsule coupled to a housing of an IMD and a source of reference potential.

FIG. 7 is a schematic illustration of a sensor capsule 17 coupled to a housing 100 of an IMD and a source of reference potential 53 according to certain embodiments of the invention described herein.

Figure 8:
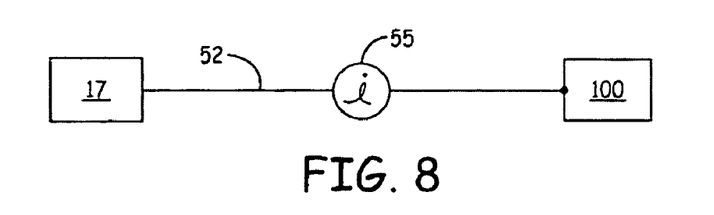
FIG. 8. is a schematic view of a sensor capsule coupled to a electrical current detector and operative circuitry housed within an IMD.

FIG. 8. is a schematic view of a sensor capsule 17 coupled to a electrical current detector 55 and operative circuitry housed within an IMD 100. As described herein in the event that excess current is detected energy for the sensor capsule 17 can be interrupted, either permanently or temporarily.

Figure 9:
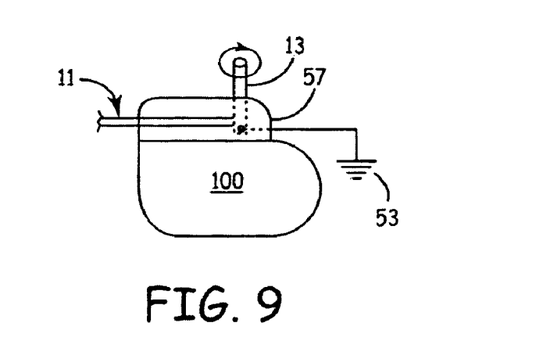
FIG. 9 is a schematic view of an IMD having a proximal lead-end set screw for mechanically retaining the proximal end of a medical electrical lead within a connector block, wherein said set screw couples to a source of reference potential.

FIG. 9 is a schematic view of an IMD 100 having a proximal lead-end set screw 13 for mechanically retaining the proximal end of a medical electrical lead 11 within a connector block 57, wherein said set screw couples to a source of reference potential 53. The set screw can also promote electrical communication between conductors on the proximal end of the lead 11 and corresponding conductive portions of the connector block 57. The conductive portions connect via hermetically sealed conductive feedthrough pins to operative circuitry within the IMD 100.

In one embodiment, an AIMD configured to chronically monitor venous pressure in the RV either: (i) selectively provide electrical energy (e.g., energy adequate to capture a cardiac chamber if provided during a non-refractory period, or on the order of two or more volts) to a pressure sensor via a medical electrical lead or (ii) blocks the output signal from the sensor during such therapy delivery to the myocardium. As a result, possible degradation of the output signal due to pacing and/or cardioversion-defibrillation therapy delivery is avoided. This aspect of the invention can be utilized in conjunction with transvenous IPGs and ICDs as well as wholly subcutaneous ICDs (e.g., a device implanted sub-muscularly or subcutaneously). The selectivity of providing power to the sensor and the duration that the output signal is blocked can be programmable or preset to nominal settings.

In the event that two separate devices are implanted (e.g., an IPG and a implantable physiologic sensor, IPS) a high impedance electrical reference for the IPS housing which couples to the IPS capsule (e.g., via a dedicated conductor or via a conductor used to power the IPS) will limit current flow from the electrical stimulation and should avoid degradation of the output signal from the IPS.

Thus, a system and method have been described which provide methods and apparatus for mitigating possible failure mechanisms for AIMDs coupled to chronically implantable sensors. Aspects of the present invention have been illustrated by the exemplary embodiments described herein. Numerous variations for providing such robust structures and methods can be readily appreciated by one having skill in the art having the benefit of the teachings provided herein. The described embodiments are intended to be illustrative of methods for practicing the invention and, therefore, should not be considered limiting with regard to the following claims.

While exemplary embodiments have been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

The invention claimed is:

1. An apparatus comprising:
   an implantable physiologic mechanical sensor for providing an output signal related to one or more physiologic parameters of a subject;
   a first electrical conductor coupled to the sensor;
   an implantable medical device comprising a pulse generator circuit adapted for delivery of therapy pulses to a portion of tissue;
   means for selectively energizing the sensor via the first electrical conductor;
   a second electrical conductor coupled to the implantable medical device and receiving the output signal from the sensor;
   an output signal processing circuit coupled to the second electrical conductor; and means for excluding signals on the second conductor from the output signal processing circuit during a temporal window corresponding to the therapy delivery of a therapy pulse.

2. An apparatus according to claim 1, wherein the mechanical sensor comprises one of an accelerometer and a pressure sensor.

3. An apparatus according to claim 1, wherein the implantable medical device comprises at least one of a cardiac pacemaker, a cardiac defibrillator, a gastric stimulator, a neurological stimulator, a brain stimulator, a skeletal muscle stimulator, a spinal cord stimulator.

4. An apparatus comprising:
an implantable physiologic sensor for providing an output signal related to one or more physiologic parameters of a subject;
a first electrical conductor coupled to the sensor;
an implantable medical device comprising a pulse generator circuit adapted for delivery of therapy pulses to a portion of tissue;
means for selectively energizing the sensor via the first electrical conductor;
a second electrical conductor coupled to the implantable medical device and receiving the output signal from the sensor;
an output signal processing circuit coupled to the second electrical conductor; and
means for excluding signals on the second conductor from the output signal processing circuit during a temporal window corresponding to the therapy delivery of a therapy pulse;
wherein the sensor comprises a blood-based sensor.

5. An apparatus comprising:
an implantable physiologic mechanical sensor for providing an output signal related to one or more physiologic parameters of a subject;
a first electrical conductor coupled to the sensor;
an implantable medical device comprising a pulse generator circuit adapted for delivery of therapy pulses to a portion of tissue;
means for selectively energizing the sensor via the first electrical conductor;
a second electrical conductor coupled to the implantable medical device and receiving the output signal from the sensor;
means for excluding the output signal during a temporal window corresponding to the therapy delivery of a therapy pulse.

6. An apparatus according to claim 5, wherein the mechanical sensor comprises one of an accelerometer and a pressure sensor.

7. An apparatus according to claim 5, wherein the implantable medical device comprises at least one of a cardiac pacemaker, a cardiac defibrillator, a gastric stimulator, a neurological stimulator, a brain stimulator, a skeletal muscle stimulator, a spinal cord stimulator.

8. An apparatus comprising:
an implantable physiologic sensor for providing an output signal related to one or more physiologic parameters of a subject;
a first electrical conductor coupled to the sensor;
an implantable medical device comprising a pulse generator circuit adapted for delivery of therapy pulses to a portion of tissue;
means for selectively energizing the sensor via the first electrical conductor; and
a second electrical conductor coupled to the implantable medical device and receiving the output signal from the sensor; and
means for excluding the output signal during a temporal window corresponding to the therapy delivery of a therapy pulse;
wherein the sensor comprises a blood-based sensor.

9. An apparatus comprising:
an implantable physiologic sensor for providing an output signal related to one or more physiologic parameters of a subject;
a first electrical conductor coupled to the sensor;
an implantable medical device comprising a pulse generator circuit adapted for delivery of therapy pulses to a portion of tissue;
means for selectively energizing the sensor via the first electrical conductor; and
a second electrical conductor coupled to the implantable medical device and receiving the output signal from the sensor; and
means for excluding the output signal during a temporal window corresponding to the therapy delivery of a therapy pulse;
wherein the sensor comprises an ion-selective electrode.

10. An apparatus for improving the accuracy of a device comprising an implantable lead comprising a physiologic mechanical sensor mounted thereon and an implantable medical device coupled to the lead, wherein:
the implantable physiologic sensor is adapted to provide an output signal related to one or more physiologic parameters of a subject;
the lead comprises a first dedicated electrical conductor coupled to the sensor;
the implantable medical device comprises one of an implantable pulse generator (IPG) circuit and an implantable cardioverter-defibrillator (ICD) circuit adapted for therapy delivery to a portion of tissue and comprising means for selectively energizing the sensor via the first electrical conductor and an output signal processing circuit;
the lead comprises a second dedicated electrical conductor coupled to the output processing circuit and receiving the output signal from the sensor; and
means for excluding the output signal on the second dedicated conductor from the output signal processing circuit during a temporal window corresponding to the therapy delivery by one of the IPG and the ICD circuits.

11. An apparatus according to claim 10, wherein the mechanical sensor comprises one of an accelerometer and a pressure sensor.

12. An apparatus according to claim 10, wherein the apparatus comprises both the IPG circuit and the ICD circuit.

13. An apparatus according to claim 10, wherein the apparatus further comprises a substance delivery device having a reservoir for retaining a substance.

14. An apparatus according to claim 13, wherein the substance comprises at least one of: a drug, a hormone, a protein, a volume of genetic material, a peptide, a volume of biological material.

15. An apparatus according to claim 10, wherein the apparatus further comprises one or more of: a gastric stimulator, a neurological stimulator, a brain stimulator, a skeletal muscle stimulator, a spinal cord stimulator, a therapeutic substance delivery device.

16. An apparatus according to claim 10, wherein the tissue comprises one of myocardial tissue, sub-muscular tissue, subcutaneous tissue.

17. An apparatus for improving the accuracy of a device comprising an implantable lead comprising a physiologic sensor mounted thereon and an implantable medical device coupled to the lead, wherein:
- the implantable physiologic sensor is adapted to provide an output signal related to one or more physiologic parameters of a subject;
- the lead comprises a first dedicated electrical conductor coupled to the sensor;
- the implantable medical device comprises one of an implantable pulse generator (IPG) circuit and an implantable cardioverter-defibrillator (ICD) circuit adapted for therapy delivery to a portion of tissue and comprising means for selectively energizing the sensor via the first electrical conductor and an output signal processing circuit;
- the lead comprises a second dedicated electrical conductor coupled to the output processing circuit and receiving the output signal from the sensor; and
- means for excluding the output signal on the second dedicated conductor from the output signal processing circuit during a temporal window corresponding to the therapy delivery by one of the IPG and the ICD circuits;
- wherein the sensor comprises a blood-based sensor.

18. An apparatus according to claim 17, wherein the blood-based sensor comprises one of: a saturated oxygen sensor, a pH sensor, a potassium-ion sensor, a calcium-ion sensor, a lactate sensor, a metabolite sensor, a blood-sugar sensor.

19. An apparatus comprising:
- a lead comprising first and second conductors and comprising an implantable physiologic sensor providing an output signal on the second conductor related to one or more physiologic parameters of a subject in response to an energizing signal on the first conductor; and
- an implantable medical device comprising:
  - a pulse generator circuit adapted for delivery of therapy pulses to a portion of tissue;
  - means for selectively providing the energizing signal to the sensor means via the first electrical conductor;
  - an output signal processing circuit coupled to the second electrical conductor; and
  - means for excluding signals on the second conductor from the output signal processing circuit during a temporal window corresponding to the therapy delivery of a therapy pulse.

20. An apparatus according to claim 19, wherein the sensor comprises a mechanical sensor.

21. An apparatus according to claim 20, wherein the mechanical sensor comprises one of an accelerometer and a pressure sensor.

22. An apparatus according to claim 19, wherein the sensor comprises a blood-based sensor.

23. An apparatus according to claim 19, wherein the implantable medical device comprises at least one of a cardiac pacemaker, a cardiac defibrillator, a gastric stimulator, a neurological stimulator, a brain stimulator, a skeletal muscle stimulator, a spinal cord stimulator.

24. An apparatus comprising:
- an implantable lead comprising first and second electrical conductors;
- an implantable medical device coupled to the first and second electrical conductors and comprising:
  - a pulse generator circuit adapted for delivery of therapy pulses to a portion of tissue;
  - means for selectively providing a energizing signal to the first electrical conductor; and
  - means for excluding signals on the second conductor from the implantable medical device during a temporal window corresponding to the therapy delivery of a therapy pulse; and
- wherein the lead further comprises an implantable physiologic sensor providing an output signal on the second conductor related to one or more physiologic parameters of a subject in response to an energizing signal on the first conductor.

25. An apparatus according to claim 24, wherein the sensor comprises a mechanical sensor.

26. An apparatus according to claim 25, wherein the mechanical sensor comprises one of an accelerometer and a pressure sensor.

27. An apparatus according to claim 24, wherein the sensor comprises a blood-based sensor.

28. An apparatus according to claim 24, wherein the sensor comprises an ion-selective electrode.

29. An apparatus according to claim 24, wherein the implantable medical device comprises at least one of a cardiac pacemaker, a cardiac defibrillator, a gastric stimulator, a neurological stimulator, a brain stimulator, a skeletal muscle stimulator, a spinal cord stimulator.

* * * * *